US00RE39233E

(19) United States
(12) Reissued Patent
McGrath

(10) Patent Number: US RE39,233 E
(45) Date of Reissued Patent: Aug. 8, 2006

(54) CONSOLIDATED MONITORING CABLE ARRANGEMENT

(76) Inventor: John E. McGrath, 16 St. Joseph St., #48, Toronto, Ontario (CA), M4Y1J9

(21) Appl. No.: 10/375,375

(22) Filed: Feb. 27, 2003

Related U.S. Patent Documents

Reissue of:
(64) Patent No.: 6,193,655
Issued: Feb. 27, 2001
Appl. No.: 08/429,298
Filed: Apr. 25, 1995

(30) Foreign Application Priority Data

Apr. 25, 1994 (GB) ..... 9408142

(51) Int. Cl.
*A61B 5/00* (2006.01)

(52) U.S. Cl. ..... 600/301; 600/481; 128/897; 439/638; 439/909

(58) Field of Classification Search ..... 600/301, 600/483, 484, 373, 481; 248/51; 439/638, 439/639, 540.1, 701, 909, 502; 128/897
See application file for complete search history.

(56) References Cited

U.S. PATENT DOCUMENTS

| | | | | | |
|---|---|---|---|---|---|
| 3,049,688 | A | * | 8/1962 | Sinopoli | 439/540.1 |
| 3,323,514 | A | * | 6/1967 | Barrett, Jr. | 600/508 |
| 3,821,496 | A | * | 6/1974 | Malone | 191/12.2 R |
| 3,910,257 | A | * | 10/1975 | Fletcher et al. | 600/483 |
| 4,103,985 | A | * | 8/1978 | Krolak et al. | 439/540.1 |
| 4,566,666 | A | * | 1/1986 | Meska et al. | 248/51 |
| 4,577,917 | A | * | 3/1986 | Nashimoto et al. | 439/638 |
| 4,648,682 | A | * | 3/1987 | Tubbs | 439/581 |
| 4,861,282 | A | * | 8/1989 | Kobayashi et al. | 439/540.1 |
| 4,864,632 | A | * | 9/1989 | Moriyama et al. | |
| 4,895,161 | A | * | 1/1990 | Cudahy et al. | 128/710 |
| 4,981,438 | A | * | 1/1991 | Bekhiet | 439/638 |
| 5,002,502 | A | * | 3/1991 | Hill | 439/540.1 |
| 5,083,238 | A | * | 1/1992 | Bousman | 439/502 |
| 5,149,277 | A | * | 9/1992 | LeMaster | |
| 5,161,997 | A | * | 11/1992 | Defibaugh et al. | 439/540.1 |
| 5,293,013 | A | * | 3/1994 | Takahashi | 439/502 |
| 5,343,869 | A | * | 9/1994 | Pross et al. | 600/301 |
| 5,375,604 | A | | 12/1994 | Kelly et al. | |
| 5,509,822 | A | * | 4/1996 | Negus et al. | 600/373 |
| 5,566,676 | A | | 10/1996 | Rosenfeldt et al. | |
| 5,685,314 | A | | 11/1997 | Geheb et al. | |
| 5,819,229 | A | * | 10/1998 | Boppe | 600/301 |
| 6,183,417 | B1 | | 2/2001 | Geheb et al. | |
| 6,221,012 | B1 | | 4/2001 | Maschke et al. | |

FOREIGN PATENT DOCUMENTS

| | | |
|---|---|---|
| CH | 524 992 | 8/1972 |
| DE | 1466807 | 5/1969 |
| DE | 8908398 | 12/1989 |
| EP | 0466272 A1 | 1/1992 |
| FR | 1531413 | 7/1968 |
| GB | 1208654 | 10/1970 |

* cited by examiner

*Primary Examiner*—Lee S. Cohen
(74) *Attorney, Agent, or Firm*—Hoffman & Baron, LLP

(57) ABSTRACT

A consolidated monitoring cable arrangement allows multiple cables extending between a surgical gurney, or other type of patient support platform, and a peripheral monitoring stand to be consolidated into a single cable. The present use of multiple cables has the disadvantage that the region between a gurney and a monitoring stand is cluttered. This can present a hazard to medical personnel, particularly when an emergency situation requires that concentration be focused on the needs of the patient. In a primary form, the subject cable arrangement uses two boxes, one on the gurney and another on the monitoring stand; a detachable cable connects the two boxes. Shorter cables of uniform length are used to connect a patient on the gurney and equipment on the monitoring stand to a respective box. Besides the aforementioned safety advantage, this cable arrangement reduces the expense of frequent replacement of damaged cables.

66 Claims, 4 Drawing Sheets

CONSOLIDATED MONITORING CABLE ARRANGEMENT

Matter enclosed in heavy brackets [ ] appears in the original patent but forms no part of this reissue specification; matter printed in italics indicates the additions made by reissue.

The invention relates to a consolidated cable arrangement, and in particular, to an arrangement which replaces multiple cables connecting multiple devices at each of two locations into a single detachable cable connectable to a bar placed at one location or at both locations.

In operating rooms and intensive care units multiple monitoring equipment cables may extend between probes secured to a patient on a surgical gurney or bed and the respective display devices supported on a peripheral stand or trolley. If anesthesia is being administered to the patient, the cables may drape across the anaesthetic equipment and make simple manoeuvering around the gurney difficult for the anaesthetist. Doctors and nurses treating the patient may have their mobility curtailed by the cables, and that could present a serious problem during an emergency. There must also be considered the further problems of untangling multiple cables, and the high cost of replacing cables that are damaged. As specialized items manufactured in limited numbers, such cables can be very expensive to replace.

Ideally one might wish to remove all of the various forms of connecting cables between a gurney and the peripheral stand that holds monitoring display equipment. That is, however, difficult to achieve. An alternate way of alleviating the problem is to consolidate all of the separate cables into a single cable that can then be strategically positioned between the gurney and the peripheral stand so as not to interfere with the movement of persons around the gurney. The subject invention is directed to the use of such a consolidated cable in association with a 'satellite bar' on the gurney. The cable may be quickly connected to, or detached from, the satellite bar which also has a series of second connection points to each of which a respective monitoring probe is connectable.

Besides the previously-mentioned advantages flowing from use of a single consolidated cable, another advantage is the ease in identifying which probes are connected to the satellite bar; that results from each connection point on the bar being labelled. An associated advantage is that cables intended to extend between the normal probe points on patients and the respective connection points on the bar may be manufactured with uniform lengths; this differs from conventional cables, which have to be sufficiently long to extend between a gurney and an associated peripheral stand. If a patient is carried on the gurney between an operating theatre and a recovery room, monitoring cables can remain connected to the patient; the satellite bar is simply connected to another peripheral stand at the new location.

In one form, the cable arrangement comprises a satellite unit adapted to be positioned on a patient support platform, a base unit adapted to be positioned on a stand peripheral to the platform, and a detachable cable adapted to connect the two units. The base unit has a series of first connection points each connectable to a respective monitoring display, and that unit also has one or more second connection points. Each one of a series of input lines of each first connection point is internally connected to one of a series of input lines of the one or more second connection points. The satellite unit has a series of third connection points each connectable to a respective monitoring probe, and that unit also has one or more fourth connection points. Each one of a series of input lines of each third connection point is internally connected to one of a series of input lines of the one or more fourth connection points. The detachable cable is adapted to connect each input line of the one or more second connection points on the base unit to a respective input line of the one or more fourth connection points on the satellite unit. With this arrangement, all of the probes are connectable to the respective displays by the cable. The region between the platform and the peripheral stand is thereby maintained in a less cluttered state than if each probe was independently connectable to the respective display.

The base unit may have only a single second connection point, and the satellite unit may have only a single fourth connection point. The patient support platform may be a surgical gurney. The cable may be detachable only from the satellite unit, or from both the base unit and the satellite unit. Each of the input lines may be adapted to carry electrical signals. The satellite unit may be secured by fastening means to the surgical gurney, and may have a series of hook members extending from it; each of those hook members is adapted to support a probe cable extending between a probe and a respective one of the third connection points on the satellite unit. The probes may involve monitoring of temperature, blood pressure, oxygen level, heart electrical activity, or other vital signs.

In another form, the cable arrangement may comprise a connection box securable by fastening means to a surgical gurney, and a detachable cable connectable to the connection box. In this arrangement, the box has a series of first plug receptacles and one or more second plug receptacles. Each of a series of input lines of each first plug receptacle is internally connected to one of a series of input lines of the one or more second plug receptacles. Each of the first plug receptacles is adapted to receive a plug from a respective patient monitoring probe. The cable has a plug on its one end adapted to connect with the one or more second plug receptacles of the connection box. The other end of the cable terminates in a series of plugs each connectable to a respective monitoring display on a peripheral stand.

The invention will next be more fully described by means of two preferred embodiments, utilizing the accompanying drawings in which.

Figure 1:
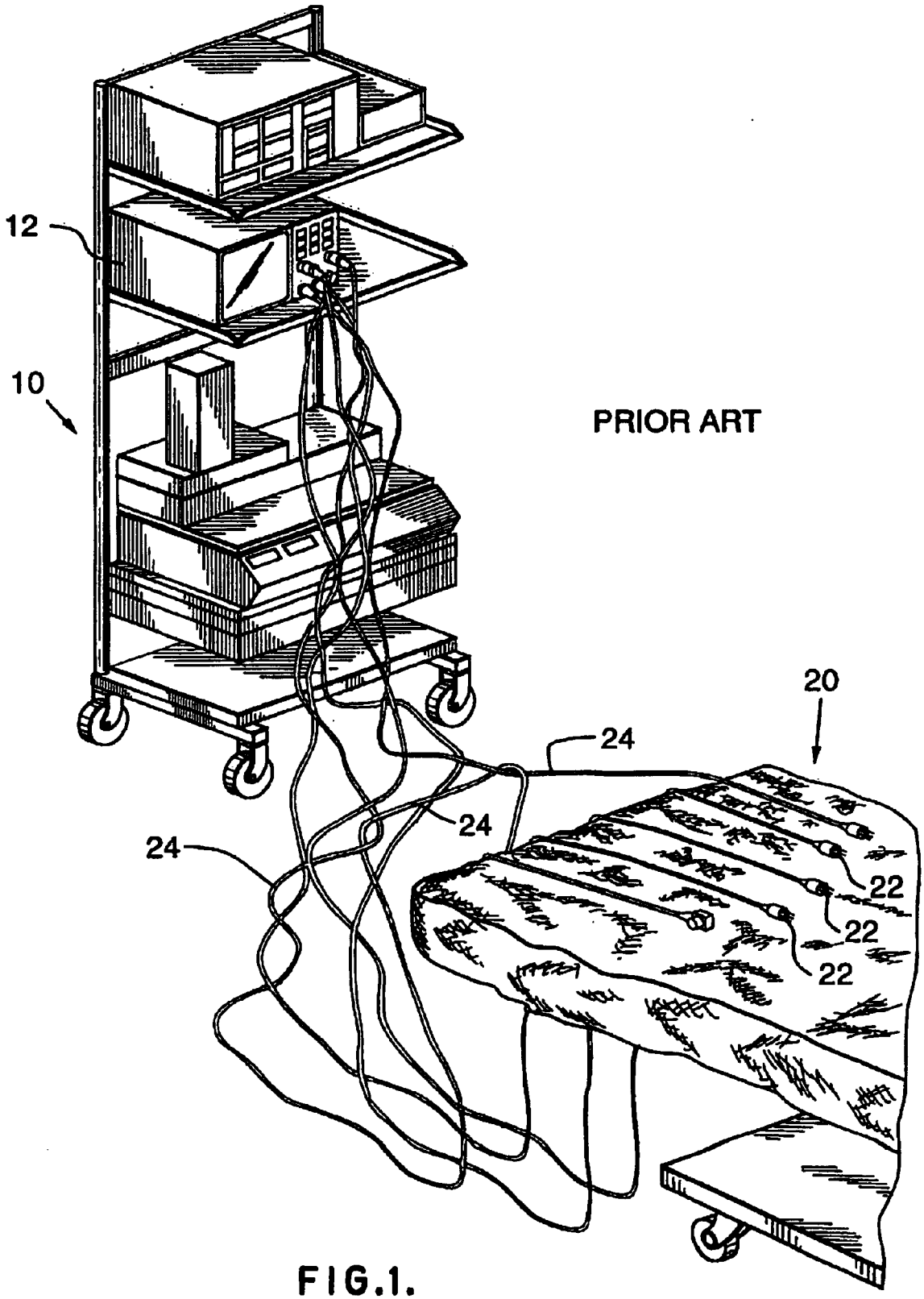
FIG. 1 is a perspective view of a surgical gurney, a portable monitoring stand, and a prior art arrangement of multiple cables extending between the gurney and the stand.

A typical existing cable arrangement between a surgical gurney and a peripheral stand supporting monitoring instrumentation is illustrated in FIG. 1. Each monitoring display on the stand has one or more cables crossing the space that separates the stand from the gurney; each cable terminates in a probe attachable to a patient lying on the gurney. In FIG. 1 a monitoring stand 10 supports a monitoring display unit 12; the same unit could, for example, display an electrocardiogram (ECG) output and a temperature output. A surgical gurney, generally designated 20, supports a series of probes 22 on the end of the cables 24 extending from the display unit; probes 22 are attachable to a patient on the gurney. Cable 24 may or may not extend to the floor; in either case, the cables represent a hazard to medical personnel attempting to move around gurney 20.

Figure 2:
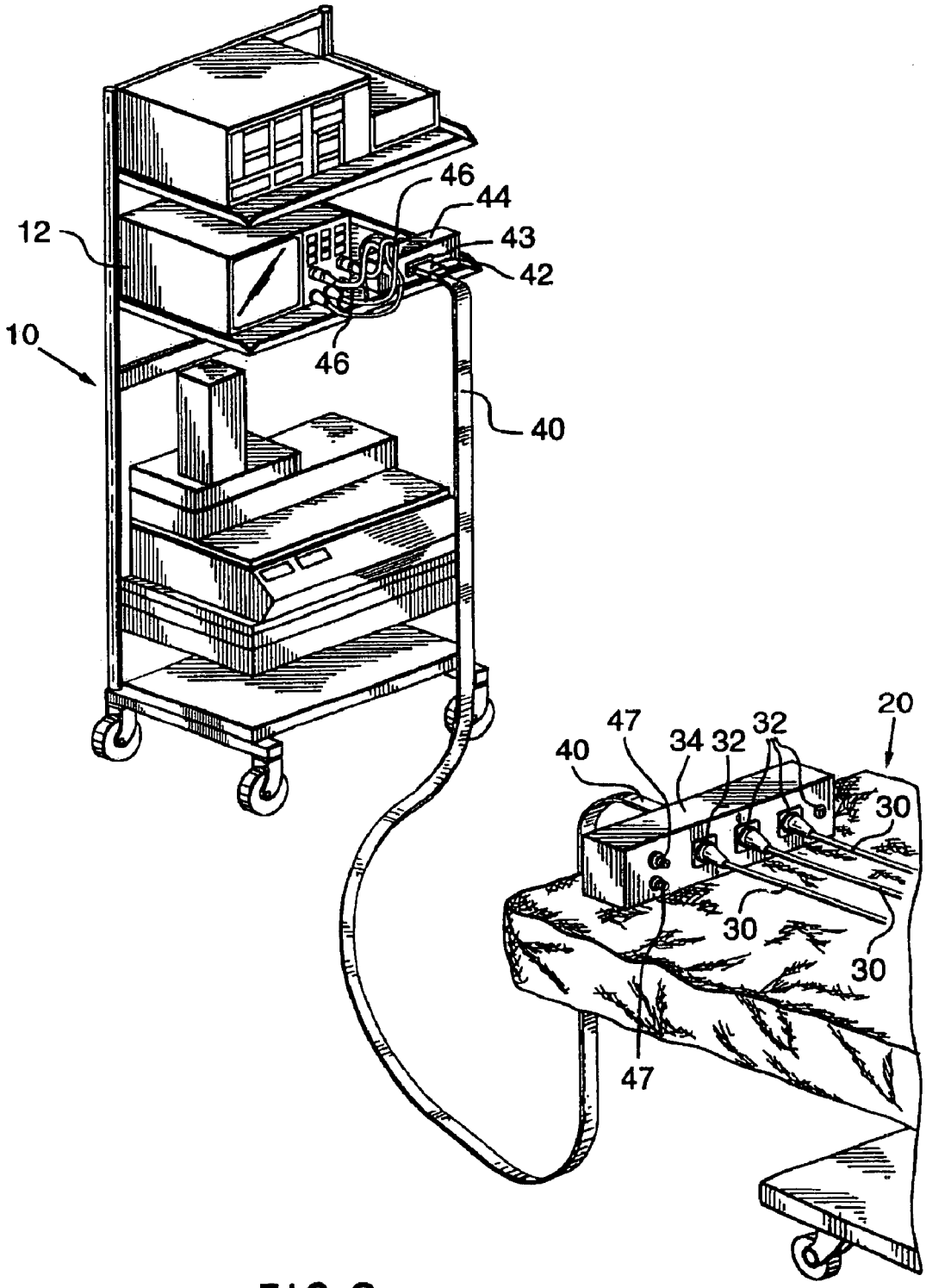
FIG. 2 is a perspective view similar to FIG. 1 but illustrating the use of the consolidated cable arrangement of the invention.
Figure 3:
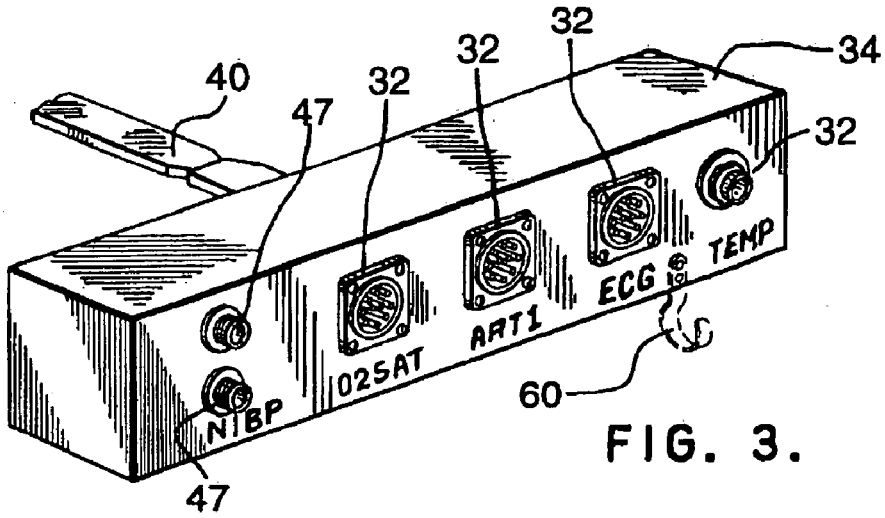
FIG. 3 is a perspective view of a box connectable to one end of the consolidated cable, the box being securable by fastening means to a surgical gurney.
Figure 4:
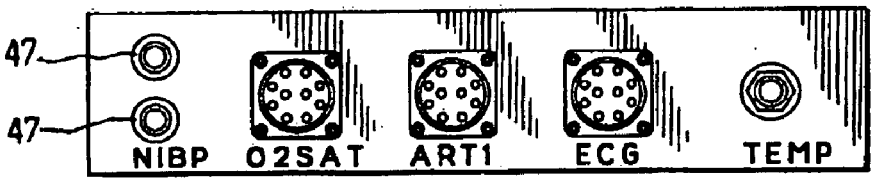
FIG. 4 is a front view of the box of FIG. 3.
Figure 5:
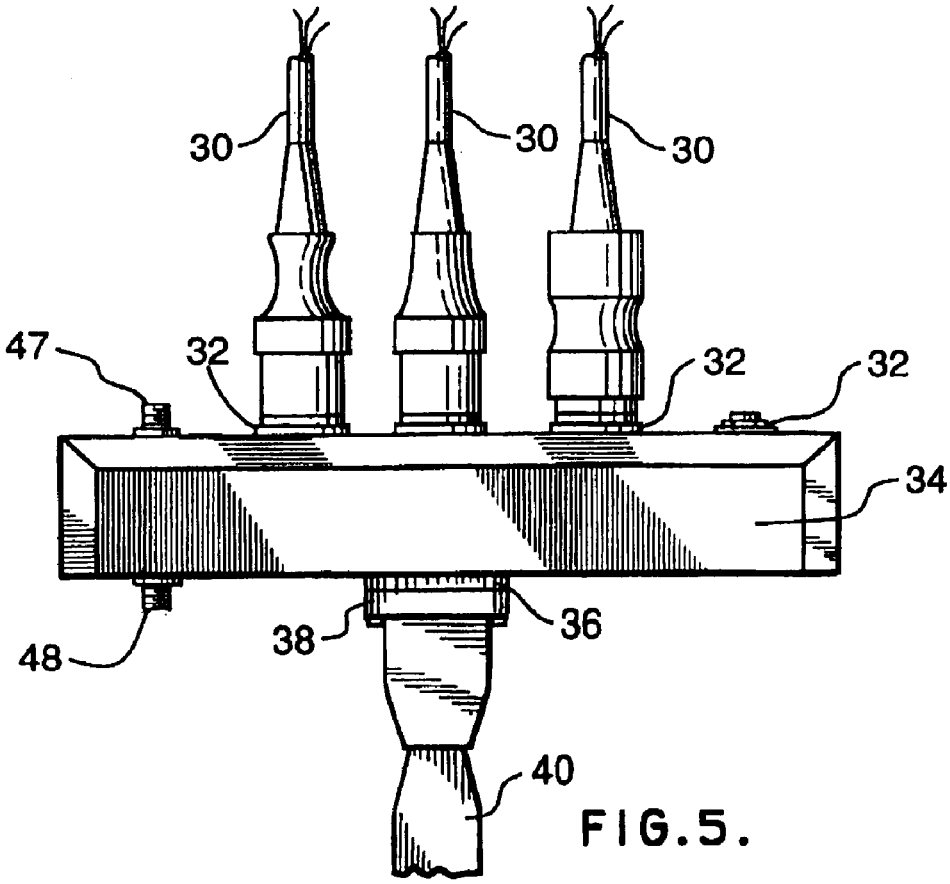
FIG. 5 is a top view of the box of FIG. 3.

FIG. 2 illustrates the use of the consolidated cable arrangement of the invention. Instead of the cables 24 of the prior art arrangement of FIG. 1, a series of cables 30 connectable to a patient on gurney 20 are each plugged into a respective receptacle 32 on a connection box 34. As shown in FIG. 3, the 4 receptacles 32 in this embodiment receive plugs from probes that monitor oxygen level, blood pressure, heart electrical activity, and body temperature. Each of the pins on each of the plugs 32 is connected inside of the connection box 34 through internal connections 35 with one of the pins of a common type of ribbon cable connector 36 positioned on a second face of connection box 34 (as shown in FIG. 4). Connector 36 is adapted to receive a plug 38 connected to one end of a ribbon cable 40. The other end of the ribbon cable 40 has a plug 42 that connects with a connector 43 on one side of a connection box 44 having a similar construction to box 34. A series of receptacles (not shown) on another side of box 44 each receives a plug connected to cables 46 extending from a respective monitoring display on unit 12.

The described cable 40 carries only electrical signal lines, but it is also possible to include in the cable thin tubing for pneumatic measurements. Above the designation 'NIBP' (Non-Invasive Blood Pressure) are a pair of threaded tubes, a first end of each tube being designated 47 and the other end being designated 48. The first end 47 would connect with a tube (not shown) to an arm cuff on a patient, and the other end 48 would connect with another tube which would be integrated into cable 40. Connection box 44 at monitoring stand 10 would have a similar pair of threaded tubes extending through it.

Although not shown, a protective plastic cover could be placed over that portion of cable 40 that extends across the floor.

Figure 6:
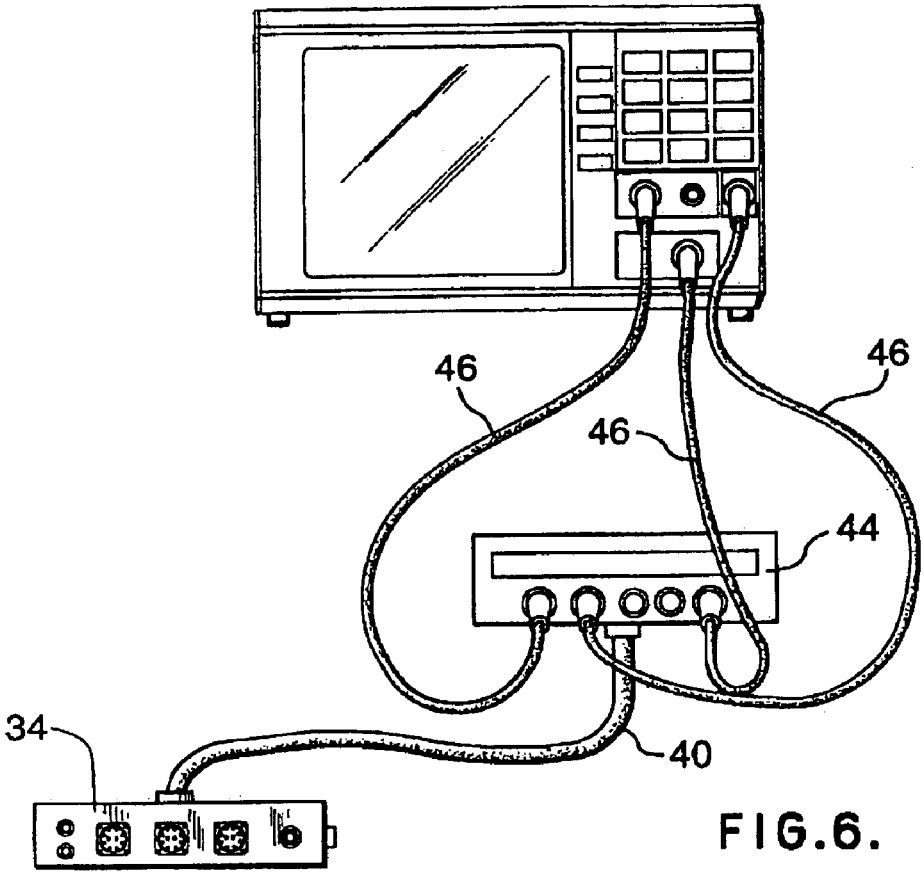
FIG. 6 illustrates a first embodiment of the consolidated cable arrangement of the invention; and, FIG. 7 illustrates a second embodiment of the consolidated cable arrangement of the invention.
Figure 7:
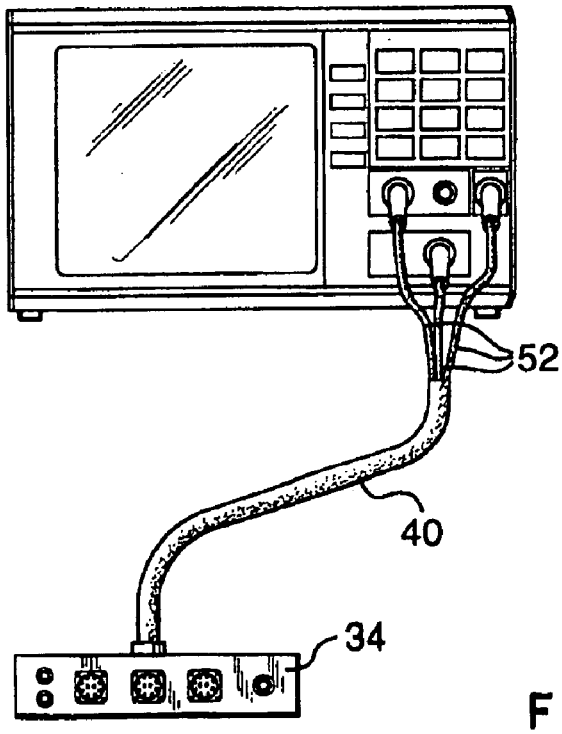

FIGS. 6 and 7 illustrate respectively the embodiment above described and a second embodiment in which the second connection box 44 on monitoring stand 10 is not used. In the second embodiment, the other end of cable 40 is 'broken out', near monitoring stand 10, into a series of cables 52 each extending to a respective monitoring display. With the first embodiment, a standard ribbon cable could be used for cable 40; with the second embodiment, cable 40 needs to be specially constructed to match the receptacles on the display unit or units to which it is to be connected.

Although the connection boxes 34 and 44 are built with receptacles corresponding to specific manufacturers' monitoring equipment, there is no difficulty in connecting the equipment of the other manufacturers by using adaptors. One of the companies that makes such adaptors is Fogg System Company, Inc. of Aurora, Colo.

As shown is FIG. 3 at 33, either of the connection boxes 34 and 44 could be fastened to the gurney 20 or the stand 10, respectively, to extend from one side. With this arrangement, a series of hooks could be built onto each box (shown in outline as 60 in FIG. 3) to support any cables plugged into receptacles on the boxes when not in use. With the subject invention, the cables 30 that are used to connect probes on the gurney 20 to connection box 34 may be made a uniform length, for example, a meter, similarly, the cables 46 used to connect the monitoring displays on stand 10 to connection box 44 may also be made a short uniform length. This obviates the current problems created when different manufacturers provide different lengths of cable with their monitoring equipment; for instance, 8 feet, 10 feet and 12 feet are common lengths for cable supplied with equipment.

What is claimed as the invention is:

1. A patient monitoring system comprising a patient support platform, a peripheral stand, *one or more* monitoring displays on the peripheral stand, monitoring probes for attaching to a patient and a cable arrangement carrying monitoring data between the patient support platform and the *one or more* monitoring displays, the cable arrangement comprising:

(a) a base unit positioned at the peripheral stand and having a series of first connection points each connected to a respective one of the *one or more* monitoring displays in the stand, the base unit also having one or more second connection points, each one of a series of input lines of each first connection point being internally connected directly to one of a series of input lines of the one or more second connection points;

(b) a satellite unit positioned on the patient support platform and having a series of third connection points each connected to a respective monitoring probe, *said satellite unit being positionable on the patient support platform independent of the positioning of the monitoring probes,* the satellite unit also having one *or* more fourth connection points, each one of a series of input lines of each third connection point being internally connected directly to one of a series of input lines of the one or more fourth connection points; and (c) a cable connecting the one or more second connection points in the base unit directly to the one or more fourth connection points on the satellite unit, the cable being readily detachable from the one or more fourth connection points;

wherein all of the probes are connected to the satellite unit over the patient support platform, all of the *one or more* monitoring displays are connected to the base unit at the peripheral stand; and the platform and stand are connected solely by said cable, the region between the patient support platform and the peripheral stand being thereby maintained in a less cluttered state than if each probe was independently connectable to the respective display.

2. A [cable arrangement] *system* as in claim 1, wherein there is only a single second connection point and a single fourth connection point.

3. A system as in claim 1, wherein the patient support platform is a surgical gurney.

4. A system as in claim 1, wherein the cable is detachable [only] from the satellite unit.

5. A system as in claim 1, wherein the cable is detachable from both the base unit and the satellite unit.

6. A system as in claim 1, wherein each of the input lines is adapted to carry electrical signals.

7. A system as in claim 1, wherein the satellite unit is secured by fastening means to the patient support [gurney] *platform.*

8. A system as in claim 1, wherein the satellite unit has a series of hook members extending therefrom, each of the hook members being adapted to support a probe cable extending between a probe and a respective one of the third connection points on the satellite unit.

9. A system as in claim 7, wherein the satellite unit has a series of hook members extending therefrom, each of the [hooked] *hook* members being adapted to support a probe cable extending between a probe and a respective one of the third connection points on the satellite unit.

10. A system as in claim 1, wherein the probes comprise temperature, blood pressure, oxygen level and heart electrical activity measurement devices.

11. A patient monitoring system comprising a patient support platform, a peripheral stand, *one or more* monitoring displays on the peripheral stand, monitoring probes for attachment to a patient, and a cable arrangement carrying monitoring data between the patient support platform and the *one or more* monitoring displays, the cable arrangement comprising:

(a) a connection box *positionable* on the patient support platform *independent of the positioning of the monitoring probes*, the box having a series of first plug receptacles and one or more second plug receptacles, each one of a series of input lines for each first plug receptacle being directly internally connected to one of a series of input lines of the one or more second plug receptacles, each of the first plug receptacles receiving a plug from a respective patient monitoring probe; and (b) a cable having a plug on its one end connected detachably with the one or more second plug receptacles of the connection box, the other end of the cable terminating in a series of plugs each connected to a respective monitoring display on the peripheral stand;

wherein all of the probes are connected to the connection box over the patient support platform, and the platform *and* stand are connected solely by the cable, the region between the patient support platform and the peripheral stand being thereby maintained in a less cluttered state than if each probe was independently connected to the respective display.

12. A system as in claim 11, wherein the patient support platform is a surgical gurney.

13. A system as in claim 11, wherein each of the input lines is adapted to carry electrical signals.

14. A system as in claim 11, wherein the connection box has a series of hook members extending therefrom, each of the hook members being adapted to support a probe cable extending between a probe and a respective one of the first plug receptacles.

15. A system as in claim 11, wherein the probes comprise temperature, blood pressure, oxygen level and heart electrical activity measurement devices.

16. A patient monitoring probe connection system used in conjunction with a patient support platform and remote monitoring equipment, said system comprising multiple probes each applied at one end to a patient on the patient support platform, a satellite connection bar on the platform establishing connections between opposite ends of the probes and the remote monitoring equipment, *said satellite connection bar being positionable on the patient support platform independent of the positioning of said probes,* said satellite connection bar comprising first external connectors for releasably receiving opposite ends of said probes over the platform, a second external connector, and internal connections within the bar directly between said [fist] *first* external connectors on the one hand and said second external connector on the other hand; and a consolidated connection cable having two ends with a connector at one end complementary to and releasably connected to said second external connector, and means at the other end connected to said remote monitoring equipment.

17. A [patient support platform according to] *system as in* claim 16, wherein the consolidated connection cable includes a connector at its other end for connection to a connection bar adjacent the monitoring equipment.

*18. A patient monitoring system comprising a patient support platform, a peripheral stand, one or more monitoring displays on the peripheral stand, monitoring probes for attaching to a patient and a cable arrangement carrying monitoring data between the patient support platform and the one or more monitoring displays, the cable arrangement comprising:*

*(a) a base unit positioned at the peripheral stand and having a series of first connection points each connected to a respective one of the one or more monitoring displays in the stand, the base unit also having one or more second connection points, each one of a series of input lines of each first connection point being internally connected directly to one of a series of input lines of the one or more second connection points;*

*(b) a satellite unit positioned on the patient support platform and having a series of third connection points each connected to a respective monitoring probe, said satellite unit being positionable on the patient support platform independent of the positioning of the monitoring probes, the satellite unit also having one or more fourth connection points, each one of a series of input lines of each third connection point being internally connected directly to one of a series of input lines of the one or more fourth connection points; and*

*(c) a cable connecting the one or more second connection points in the base unit directly to the one or more fourth connection points on the satellite unit;*

*wherein all of the probes are connected to the satellite unit over the patient support platform, all of the one or more monitoring displays are connected to the base unit at the peripheral stand; and the platform and stand are connected solely by said cable, the region between the patient support platform and the peripheral stand being thereby maintained in a less cluttered state than if each probe was independently connectable to the respective display.*

*19. A system as in claim 18, wherein the cable is detachable from the base unit.*

*20. A system as in claim 18, wherein there is only a single second connection point and a single fourth connection point.*

*21. A system as in claim 18, wherein the patient support platform is a surgical gurney.*

*22. A system as in claim 18, wherein each of the input lines is adapted to carry electrical signals.*

*23. A system as in claim 18, wherein the satellite unit is secured by fastening means to the patient support platform.*

*24. A system as in claim 18, wherein the satellite unit has a series of hook members extending therefrom, each of the hook members being adapted to support a probe cable extending between a probe and a respective one of the third connection points on the satellite unit.*

*25. A system as in claim 23, wherein the satellite unit has a series of hook members extending therefrom, each of the hook members being adapted to support a probe cable extending between a probe and a respective one of the third connection points on the satellite unit.*

*26. A system as in claim 18, wherein the probes comprise temperature, blood pressure, oxygen level and heart electrical activity measurement devices.*

*27. A system as in claim 18, wherein the cable includes tubing connected to said base unit and said satellite unit, said tubing having a passage being formed therethrough to allow for fluid flow.*

*28. A system as in claim 18 further comprising a protective plastic cover placed over a portion of said cable.*

*29. A patient monitoring system comprising a patient support platform, a peripheral stand, one or more monitoring displays on the peripheral stand, monitoring probes for attachment to a patient, and a cable arrangement carrying monitoring data between the patient support platform and the one or more monitoring displays, the cable arrangement comprising:*

*(a) a connection box positionable on the patient support platform independent of the positioning of the monitoring probes, the box having a series of first plug receptacles, each of the first plug receptacles being formed to receive a plug from a respective patient monitoring probe; and*

*(b) a cable connected to the connection box, the other end of the cable being connectable to said one or more monitoring displays on the peripheral stand;*

*wherein all of the probes are connected to the connection box over the patient support platform, and the platform and stand are connected solely by the cable, the region between the patient support platform and the peripheral stand being thereby maintained in a less cluttered state than if each probe was independently connected to the respective display.*

*30. A system as in claim 29, wherein the cable is detachable from said one or more monitoring displays.*

*31. A system as in claim 29, wherein the cable is detachable from the connection box and said one or more monitoring displays.*

*32. A system as in claim 29, wherein the patient support platform is a surgical gurney.*

*33. A system as in claim 29, wherein the cable is adapted to carry electrical signals.*

*34. A system as in claim 29, wherein the connection box has a series of hook members extending therefrom, each of the hook members being adapted to support a probe cable extending between a probe and a respective one of the first plug receptacles.*

*35. A system as in claim 29, wherein the probes comprise temperature, blood pressure, oxygen level and heart electrical activity measurement devices.*

*36. A system as in claim 29, wherein the cable includes tubing, said tubing having a passage formed therethrough to allow for fluid flow.*

*37. A system as in claim 29 further comprising a protective plastic cover placed over a portion of said cable.*

*38. A patient monitoring probe connection system used in conjunction with a patient support platform and remote monitoring equipment, said system comprising multiple probes each applied at one end to a patient on the patient support platform, a satellite connection bar on the platform establishing connections between opposite ends of the probes and the remote monitoring equipment, said satellite connection bar being positionable on the patient support platform independent of the positioning of said probes, said satellite connection bar comprising first external connectors for releasably receiving opposite ends of said probes over the platform; and*

*a consolidated connection cable having one end connected to said satellite connection bar, and means at the other end connected to said remote monitoring equipment, wherein said consolidated connection cable is directly connected to said first external connectors via internal connections in said satellite connection bar.*

*39. A system as in claim 38, wherein the consolidated connection cable is detachable from said remote monitoring equipment.*

*40. A system as in claim 38, wherein the consolidated connection cable is detachable from said satellite connection bar and said remote monitoring equipment.*

*41. A system as in claim 38, wherein the consolidated connection cable includes a connector at its other end for connection to a connection bar adjacent the monitoring equipment.*

*42. A patient monitoring cable arrangement comprising:*

*(a) a cable having one or more data paths for use in connecting one or more patient probes with one or more monitors;*

*(b) a base unit at one end of said cable and being connectable to said one or more monitors to connect said one or more data paths to said one or more monitors; and*

*(c) a satellite unit at the other end of said cable being connectable to said one or more patient probes to connect said one or more data paths with said one or more patient probes, said satellite unit being positionable independent of the positioning of said one or more patient probes.*

*43. A patient monitoring cable arrangement as in claim 42, wherein said cable can be detached from said satellite unit.*

*44. A patient monitoring cable arrangement as in claim 42, wherein said cable can be detached from said base unit.*

*45. A patient monitoring cable arrangement as in claim 42, wherein said cable can be detached from said satellite unit and said base unit.*

*46. A patient monitoring cable arrangement comprising:*

*(a) a cable having one or more data paths for use in connecting one or more patient probes with one or more monitors, said cable having a first end and a second end, said first end of said cable being connectable to said one or more monitors to connect said one or more data paths to said one or more monitors; and*

*(b) a satellite unit at said second end of said cable being connectable to said one or more patient probes to connect said one or more data paths with said one or more patient probes, said satellite unit being positionable independent of the positioning of said one or more patient probes.*

*47. A patient monitoring cable arrangement as in claim 46, wherein said first end of said cable terminating in a series of plugs each connectable to said one or more monitors.*

*48. A patient monitoring cable arrangement as in claim 46, wherein said cable can be detached from said satellite unit.*

*49. A patient monitoring cable arrangement as in claim 46, wherein said cable can be detached from said one or more monitors.*

*50. A patient monitoring cable arrangement as in claim 46, wherein said cable can be detached from said satellite unit and said one or more monitors.*

*51. A method for monitoring data collected by monitoring probes on a patient, comprising:*

*(a) positioning a connection box on a patient support platform;*

*(b) applying at least one monitoring probe to the patient, said at least one monitoring probe being positioned independently from the position of said connection box;*

*(c) connecting said at least one monitoring probe to said connection box; and*

*(d) connecting said connection box to monitoring equipment peripheral to said patient support platform to*

*monitor or display data collected by said at least one monitoring probe.*

*52. A method as in claim 51, wherein said monitoring equipment includes at least one monitoring display.*

*53. A method as in claim 51, wherein the step of connecting said connection box to said monitoring equipment includes connecting a cable from said connection box directly to said monitoring equipment, wherein said cable includes one or more data paths associated with each said monitoring probe for carrying data from said connection box to said monitoring equipment.*

*54. A method as in claim 53, wherein said cable is detachably connected to said connection box.*

*55. A method as in claim 53, wherein said cable is detachably connected to said monitoring equipment.*

*56. A method as in claim 53, wherein said cable is detachably connected to said connection box and said monitoring equipment.*

*57. A method as in claim 51, wherein the step of connecting said connection box to said monitoring equipment includes connecting a cable from said connection box directly to a base unit, and connecting said base unit to said monitoring equipment, wherein said cable includes one or more data paths associated with each said monitoring probe for carrying data from said connection box to said base unit.*

*58. A method as in claim 57, wherein said cable is detachably connected to said connection box.*

*59. A method as in claim 57, wherein said cable is detachably connected to said base unit.*

*60. A method as in claim 57, wherein said cable is detachably connected to said connection box and said base unit.*

*61. A method as in claim 57, wherein said cable is a single cable between said connection box and said base unit.*

*62. A method as in claim 51, wherein said patient support platform is a surgical gurney.*

*63. A system as in claim 1, wherein said base unit is separate from the one or more monitoring displays.*

*64. A system as in claim 18, wherein said base unit is separate from the one or more monitoring displays.*

*65. A patient monitoring cable arrangement as in claim 42, wherein said base unit is separate from said one ore more monitors.*

*66. A method as in claim 57, wherein said base unit is separate from said monitoring equipment.*

* * * * *